(12) United States Patent
Matsuura et al.

(10) Patent No.: US 10,065,917 B2
(45) Date of Patent: Sep. 4, 2018

(54) METHOD FOR PURIFYING ACRYLIC ACID DERIVATIVE

(71) Applicant: DAIKIN INDUSTRIES, LTD., Osaka (JP)

(72) Inventors: Makoto Matsuura, Osaka (JP); Yosuke Kishikawa, Osaka (JP); Asako Yoshiyama, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/749,185

(22) PCT Filed: Aug. 5, 2016

(86) PCT No.: PCT/JP2016/073208
§ 371 (c)(1),
(2) Date: Jan. 31, 2018

(87) PCT Pub. No.: WO2017/026423
PCT Pub. Date: Feb. 16, 2017

(65) Prior Publication Data
US 2018/0222843 A1 Aug. 9, 2018

(30) Foreign Application Priority Data
Aug. 7, 2015 (JP) ................ 2015-157787

(51) Int. Cl.
*C07C 67/60* (2006.01)
*C07C 67/54* (2006.01)
*C07C 69/653* (2006.01)
*C07C 69/54* (2006.01)
*C07C 51/367* (2006.01)

(52) U.S. Cl.
CPC .......... *C07C 67/60* (2013.01); *C07C 67/54* (2013.01); *C07C 69/54* (2013.01); *C07C 69/653* (2013.01); *C07C 51/367* (2013.01)

(58) Field of Classification Search
CPC ......... C07C 67/54; C07C 67/60; C07C 69/54; C07C 69/653; C07C 51/367
See application file for complete search history.

(56) References Cited

U.S. PATENT DOCUMENTS

| | | | | |
|---|---|---|---|---|
| 5,342,487 A * | 8/1994 | McDade | ............... | C07C 67/54 203/34 |
| 6,281,386 B1 * | 8/2001 | Fauconet | ............... | C07C 51/48 562/600 |
| 2004/0204608 A1 * | 10/2004 | Yada | ............... | B01D 1/225 562/600 |
| 2005/0115590 A1 * | 6/2005 | Schroeder | ............... | B08B 9/08 134/34 |
| 2007/0244338 A1 * | 10/2007 | Funakoshi | ............... | C07C 17/275 560/219 |
| 2009/0030165 A1 * | 1/2009 | Benderly | ............... | C07C 51/44 526/77 |
| 2011/0009663 A1 * | 1/2011 | Wenger | ............... | C07C 67/60 560/174 |
| 2012/0059187 A1 | 3/2012 | Ishii et al. | | |
| 2012/0283468 A1 | 11/2012 | Kreis et al. | | |
| 2014/0200366 A1 * | 7/2014 | Curtis | ............... | C07C 67/54 562/600 |
| 2015/0191413 A1 | 7/2015 | Ohtsuka et al. | | |

FOREIGN PATENT DOCUMENTS

| | | |
|---|---|---|
| JP | 2011-1340 | 1/2011 |
| JP | 2012-530756 | 12/2012 |
| JP | 2014-62092 | 4/2014 |

OTHER PUBLICATIONS

International Search Report dated Oct. 4, 2016 in International (PCT) Application No. PCT/JP2016/073208.

* cited by examiner

*Primary Examiner* — Yate' K Cutliff
(74) *Attorney, Agent, or Firm* — Wenderoth, Lind & Ponack, L.L.P.

(57) ABSTRACT

The problem solved by the present invention is to provide a method for efficiently purifying acrylic acid derivative (I), more specifically a method for efficiently eliminating alcohol (II) from a composition containing acrylic acid derivative (I) and alcohol (II). This problem is solved by a method for purifying an acrylic acid derivative represented by Formula (I):

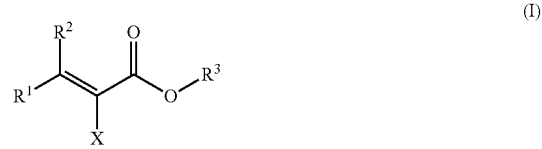

(I)

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may have one or more substituents, or hydrogen, and
X represents alkyl, fluoroalkyl, halogen, or hydrogen,
the method comprising
step A of bringing composition A containing the acrylic acid derivative represented by Formula (I) and alcohol represented by Formula (II):

$$R^4\text{—OH},$$

wherein $R^4$ represents $C_{1-6}$ alkyl,
into contact with an acid anhydride to convert the alcohol into an ester compound that has a boiling point higher than the boiling point of the acrylic acid derivative represented by Formula (I).

13 Claims, No Drawings

METHOD FOR PURIFYING ACRYLIC ACID DERIVATIVE

TECHNICAL FIELD

The present invention relates to a method for purifying an acrylic acid derivative, in particular a method for purifying an acrylic acid derivative, the method comprising eliminating alcohol from a composition containing an acrylic acid derivative and alcohol.

BACKGROUND ART

Acrylic acid derivatives are widely used for (1) materials of water-absorbing polymers; (2) materials of acrylic resins as a substitute for inorganic glass for use in window materials for buildings and vehicles, coverings for lighting equipment, lantern signs, road signs, daily necessities, office supplies, crafts, windscreens of watches, and the like; and (3) acrylic resin coating materials. Among acrylic acid derivatives, fluorine-containing acrylic acid derivatives are useful as synthetic intermediates of pharmaceuticals (e.g., antibiotics), synthetic intermediates for sheath materials of optical fibers, synthetic intermediates of coating materials, synthetic intermediates of semiconductor resist materials, and monomers of functional polymers.

Examples of known methods for producing an acrylic acid derivative include a method of producing an acrylic acid derivative by oxidizing isobutylene or propylene, and a method of producing an acrylic acid derivative using ethylene, propyne, or the like as a starting material using a transition metal catalyst.

Further, as examples of methods for producing a fluorine-containing acrylic acid derivative, Patent Document 1, for example, discloses a method of reacting a 2-fluoropropionic ester with a nitrogen-bromine-bond-containing brominating agent in the presence of a radical initiator, and Patent Document 2 discloses a process for converting a 3-halo-2-fluoropropionic acid derivative to a substituted 2-fluoroacrylic acid derivative in the presence of at least one kind of base and at least one kind of polymerization inhibitor. Patent Document 3 discloses a process for producing a compound represented by formula (1):

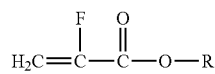
(1)

wherein R represents alkyl that may be substituted with one or more fluorine atoms, the process comprising step A of reacting a compound represented by formula (2):

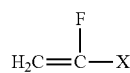
(2)

wherein X represents a bromine atom or a chlorine atom with alcohol represented by formula (3):

 (3)

wherein R represents alkyl that may be substituted with one or more fluorine atoms, and carbon monoxide in the presence of a transition metal catalyst and a base to thereby obtain the compound represented by formula (1).

CITATION LIST

Patent Documents

Patent Document 1: JP2011-001340A
Patent Document 2: JP2012-530756A
Patent Document 3: JP2014-062092A

SUMMARY OF INVENTION

Technical Problem

In the production of an acrylic acid derivative, alcohol can undesirably coexist in a target acrylic acid derivative-containing composition.

Such alcohol may possibly cause an adverse effect on desired reactions when the acrylic acid derivative is used, for example, in the applications mentioned above, i.e., synthetic intermediates of pharmaceuticals (e.g., antibiotics), synthetic intermediates for sheath materials of optical fibers, synthetic intermediates of coating materials, synthetic intermediates of semiconductor resist materials, and monomers of functional polymers.

In this case, elimination of alcohol from the composition containing the acrylic acid derivative and alcohol is necessary.

An object of the present invention is to provide a method for efficiently purifying acrylic acid derivative (I), more specifically a method for efficiently eliminating alcohol from a composition containing acrylic acid derivative (I) and alcohol.

Generally, to eliminate impurities from a useful compound, the following are examples of possible methods: (1) a method for directly eliminating the impurities; and (2) a method for eliminating the impurities by converting the impurities to other compounds through a reaction with other components.

However, the method (1) above can fail to directly eliminate the impurities with a commonly used method such as distillation, since the structures and physical properties of the useful compound and impurities are often similar.

Although the method (2) above may not suffer from this problem, the method (2) can have a problem such that the other components themselves and/or the other compounds may become new impurities. This problem, in particular, is a serious issue in fields that require extremely high purity, such as in the production of medicinal drugs or electronic materials. In these fields, therefore, the method (2) is likely to be avoided.

Accordingly, an object of the present invention is to provide a novel, highly efficient method for purifying an acrylic acid derivative while greatly reducing the incorporation of new impurities, such as those described above.

Solution to Problem

As a result of extensive research, the present inventors found that the following method can solve the above problems:

A method for purifying an acrylic acid derivative (in this specification, this derivative may sometimes be referred to as "acrylic acid derivative (I)") represented by Formula (I):

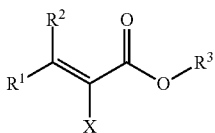
(I)

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may have one or more substituents, or hydrogen, and
X represents alkyl, fluoroalkyl, halogen, or hydrogen,
the method comprising:
step A of bringing composition A containing the acrylic acid derivative represented by Formula (I) and alcohol (in this specification, this alcohol may sometimes be referred to as "alcohol (II)") represented by Formula (II):

$R^4$—OH wherein $R^4$ represents alkyl, fluoroalkyl, or aryl that may have one or more substituents,
into contact with an acid anhydride (in this specification, this acid anhydride may sometimes be referred to as "acid anhydride (III-0)") to convert the alcohol represented by Formula (II) into an ester compound (in this specification, this ester compound may sometimes be referred to as "ester compound (IV)") that has a boiling point higher than the boiling point of the acrylic acid derivative represented by Formula (I); and
step B of separating the acrylic acid derivative represented by Formula (I) and the ester compound by distillation.

The present invention has thus been accomplished.

The present invention encompasses the following embodiments.

Item 1. A method for purifying an acrylic acid derivative represented by Formula (I):

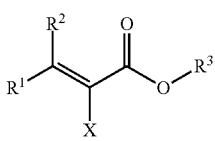
(I)

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may have one or more substituents, or hydrogen, and
X represents alkyl, fluoroalkyl, halogen, or hydrogen,
the method comprising
step A of bringing a composition A containing the acrylic acid derivative represented by Formula (I) and alcohol represented by Formula (II):

$R^4$—OH, wherein $R^4$ represents alkyl, fluoroalkyl, or aryl that may have one or more substituents,
into contact with an acid anhydride to convert the alcohol into an ester compound that has a boiling point higher than the boiling point of the acrylic acid derivative represented by Formula (I).

Item 2. The method according to Item 1, further comprising step B of separating the acrylic acid derivative represented by Formula (I) and the ester compound by distillation.

Item 3. The method according to Item 1 or 2, wherein $R^1$ represents hydrogen, $C_{1-20}$ alkyl, or $C_{1-20}$ fluoroalkyl.

Item 4. The method according to any one of Items 1 to 3, wherein $R^2$ represents hydrogen, $C_{1-20}$ alkyl, or $C_{1-20}$ fluoroalkyl.

Item 5. The method according to any one of Items 1 to 4, wherein $R^3$ represents $C_{1-20}$ linear alkyl.

Item 6. The method according to any one of Items 1 to 5, wherein X represents $C_{1-20}$ alkyl, fluorine, chlorine, or hydrogen.

Item 7. The method according to any one of Items 1 to 6, wherein $R^4$ represents $C_{1-6}$ alkyl.

Item 8. The method according to any one of Items 1 to 7, wherein the acid anhydride is a cyclic acid anhydride.

Item 9. The method according to Item 8, wherein the acid anhydride is a compound represented by Formula (III-a):

(III-a)

wherein $R^5$ represents divalent hydrocarbon.

Item 10. The method according to Item 9, wherein the acid anhydride is succinic anhydride or phthalic anhydride.

Item 11. The method according to any one of Items 1 to 10, wherein the composition A further contains a heteroatom-containing organic solvent, and wherein a composition B containing the acrylic acid derivative represented by Formula (I) and the heteroatom-containing organic solvent is obtained after the separation in step B.

Item 12. The method according to Item 11, wherein the heteroatom-containing organic solvent is separated and recovered from the composition B.

Item 13. A method for producing an acrylic acid derivative represented by Formula (I):

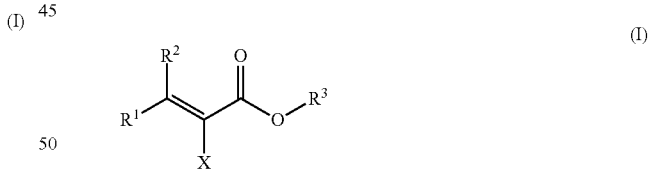
(I)

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may be substituted with one or more substituents, or hydrogen, and
X represents alkyl, fluoroalkyl, halogen, or hydrogen,
the method comprising purifying the acrylic acid derivative represented by Formula (I) by the purification method of any one of Items 1 to 12.

Advantageous Effects of Invention

The present invention provides a method for efficiently purifying acrylic acid derivative (I), more specifically a method for efficiently eliminating alcohol (II) from a composition containing acrylic acid derivative (I) and alcohol (II).

DESCRIPTION OF EMBODIMENTS

Terms

The symbols and the abbreviations in this specification are to be interpreted as having the general meanings in the related technical field to which the present invention pertains, according to the context of this specification, unless otherwise specified.

In this specification, the term "comprise/contain" encompasses the meanings of "consist essentially of" and "consist of."

In this specification, "room temperature" refers to a temperature in a range of 10 to 40° C.

In this specification, steps, treatments, or operations are performed at a room temperature, unless otherwise specified.

In this specification, "monovalent hydrocarbon" may have a linear, branched, or cyclic structure. Alternatively, the "monovalent hydrocarbon" may have a combination of these structures.

In this specification, "monovalent hydrocarbon" may be saturated or unsaturated monovalent hydrocarbon.

In this specification, examples of the monovalent hydrocarbon include alkyl and alkenyl.

In this specification, "alkyl" (the term "alkyl" encompasses the "alkyl" moiety in "fluoroalkyl" or the like) may be cyclic, linear, or branched.

In this specification, "alkyl" may be, for example, $C_{1-20}$, $C_{1-12}$, $C_{1-6}$, $C_{1-4}$, or $C_{1-3}$ alkyl.

In this specification, specific examples of "alkyl" include methyl, ethyl, propyl, isopropyl, butyl, isobutyl, sec-butyl, tert-butyl, pentyl, neopentyl, hexyl, and like linear or branched alkyl groups.

In this specification, specific examples of "alkyl" include cyclopropyl, cyclobutyl, cyclopentyl, cyclohexyl, and like $C_{3-6}$ cyclic alkyl (cycloalkyl) groups.

In this specification, "fluoroalkyl" refers to alkyl in which at least one hydrogen is replaced by fluorine.

In this specification, the number of fluorine atoms in the "fluoroalkyl" may be one or more (e.g., 1 to 3, 1 to 6, 1 to 12, or 1 to the maximum replaceable number).

In this specification, examples of "fluoroalkyl" include $C_{1-20}$, $C_{1-12}$, $C_{1-6}$, $C_{1-4}$, and $C_{1-3}$ fluoroalkyl groups.

In this specification, "fluoroalkyl" may be linear or branched.

In this specification, specific examples of "fluoroalkyl" include fluoromethyl, difluoromethyl, trifluoromethyl, 2,2,2-trifluoroethyl, pentafluoroethyl, tetrafluoropropyl (e.g., $HCF_2CF_2CH_2-$), hexafluoropropyl (e.g., $(CF_3)_2CH-$), nonafluorobutyl, octafluoropentyl (e.g., $HCF_2CF_2CF_2CF_2CH_2-$), tridecafluorohexyl, and the like.

In this specification, examples of "alkenyl" include $C_{2-20}$, $C_{2-12}$, $C_{2-6}$, $C_{2-4}$, and $C_{2-3}$ alkenyl groups.

In this specification, specific examples of "alkenyl" include vinyl, 1-propen-1-yl, 2-propen-1-yl, isopropenyl, 2-buten-1-yl, 4-penten-1-yl, 5-hexen-1-yl, and like linear or branched $C_{2-10}$ alkenyl groups.

In this specification, examples of "aryl" include phenyl and naphthyl.

In this specification, examples of "halogen" include fluorine, chlorine, bromine, and iodine.

In this specification, "alkoxy" is an alkyl-O— group.

In this specification, examples of "acyl" include alkanoyl (i.e., alkyl-CO— group).

In this specification, examples of "ester" include alkyl-carbonyloxy (i.e., alkyl-CO—O— group), alkoxycarbonyl (i.e., alkyl-O—CO— group), and the like.

In this specification, "divalent hydrocarbon" may have a linear, branched, or cyclic structure. Alternatively, "divalent hydrocarbon" may have a combination of these structures.

In this specification, "divalent hydrocarbon" may be saturated or unsaturated divalent hydrocarbon.

In this specification, examples of "divalent hydrocarbon" include $C_{1-10}$ alkylene, $C_{2-10}$ alkenylene, $C_{6-12}$ arylene, $C_{3-12}$ cycloalkylene, $C_{3-12}$ cycloalkenylene, and the like.

When the "divalent hydrocarbon" above partially or entirely has a cyclic structure, the ring in the cyclic structure may be an aromatic ring (e.g., benzene ring) or a non-aromatic ring.

Method for Purifying Acrylic Acid Derivative (I)

The method for purifying acrylic acid derivative (I) of the present invention is described in detail below.

In the purification method of the present invention, at least a portion of alcohol (II) is eliminated from composition A containing acrylic acid derivative (I) as a principal component and alcohol (II) as an impurity (i.e., a roughly purified acrylic acid derivative (I)) to obtain a purified acrylic acid derivative (I).

Purification Target

The object to be purified by the purification method of the present invention is acrylic acid derivative (I) described above.

Each symbol in Formula (I) representing acrylic acid derivative (I) is explained below.

Preferable examples of the substituents of the "aryl that may have one or more substituents" represented by $R^1$, $R^2$, or $R^3$ include fluorine, alkyl, alkoxy, acyl, ester, cyano, nitro, and fluoroalkyl. More preferable examples include fluorine.

The number of "the substituents" is preferably 0 (i.e., unsubstituted), 1, 2, or 3.

$R^1$ is preferably hydrogen, $C_{1-20}$ (preferably $C_{1-12}$, more preferably $C_{1-6}$, further preferably $C_{1-4}$, further more preferably $C_{1-3}$, particularly preferably $C_1$ or $C_2$) alkyl, or $C_{1-20}$ fluoroalkyl, and more preferably hydrogen.

$R^2$ is preferably hydrogen, $C_{1-20}$ (preferably $C_{1-12}$, more preferably $C_{1-6}$, further preferably $C_{1-4}$, further more preferably $C_{1-3}$, particularly preferably $C_1$ or $C_2$) alkyl, or $C_{1-20}$ (preferably $C_{1-12}$, more preferably $C_{1-6}$, further preferably $C_{1-4}$, further more preferably $C_{1-3}$, particularly preferably $C_1$ or $C_2$) fluoroalkyl, and more preferably hydrogen.

$R_3$ is preferably $C_{1-20}$ (preferably $C_{1-12}$, more preferably $C_{1-6}$, further preferably $C_{1-4}$, further more preferably $C_{1-3}$, particularly preferably $C_1$ or $C_2$) linear alkyl, more preferably methyl or ethyl, and further more preferably methyl.

X is preferably $C_{1-20}$ (preferably $C_{1-12}$, more preferably $C_{1-6}$, further preferably $C_{1-4}$, further more preferably $C_{1-3}$, particularly preferably $C_1$ or $C_2$) alkyl, fluorine, chlorine, or hydrogen, more preferably methyl, hydrogen, or fluorine, and further more preferably fluorine.

In Formula (I), $R^3$ is preferably $C_{1-20}$ (preferably $C_{1-12}$, more preferably $C_{1-6}$, further preferably $C_{1-4}$, further more preferably $C_{1-3}$, particularly preferably $C_1$ or $C_2$) linear alkyl, and X is preferably methyl or fluorine; and $R^3$ is more preferably methyl or ethyl (and further more preferably methyl), and X is more preferably methyl or fluorine.

In Formula (I), $R^1$ is preferably hydrogen, $R^2$ is preferably hydrogen, $R^3$ is preferably methyl or ethyl (and more preferably methyl), and X is preferably methyl, hydrogen, or fluorine (and more preferably fluorine).

In the present invention, acrylic acid derivative (I) may be a single kind, or a combination of two or more kinds.

Acrylic acid derivative (I) preferably has a boiling point within a range of 30 to 160° C., more preferably within a range of 50 to 130° C., and further more preferably within a range of 60 to 110° C.

Elimination Target in Purification

The elimination target in the purification method of the present invention is alcohol (II). The purification method of the present invention eliminates at least a portion of alcohol (II). In this purification, a larger amount of alcohol (II) is preferably eliminated.

In the purification method of the present invention, other impurities may be eliminated together with alcohol (II).

Target Material

The target material of the purification method of the present invention is composition A containing acrylic acid derivative (I) and alcohol (II) (i.e., roughly purified acrylic acid derivative (I)).

Alcohol (II) may be derived from acrylic acid derivative (I). For example, alcohol (II) may be a hydrolysate of acrylic acid derivative (I). $R^4$ may be the same as $R^3$.

The symbol in Formula (II) representing alcohol (II) is explained below.

$R^4$ is preferably alkyl, more preferably $C_{1-6}$ alkyl, and further more preferably methyl or ethyl. Specifically, in a particularly preferable embodiment according to the present invention, the alcohol represented by Formula (II) is preferably methanol or ethanol.

In the present invention, alcohol (II) may be a single kind, or a combination of two or more kinds of alcohol (II).

The production method for composition A, which is the target material of the purification method of the present invention, and the origin of composition A are not particularly limited.

Acrylic acid derivative (I) contained in composition A may be a reaction product.

Alcohol (II) contained in composition A may be, for example, a reaction solvent for the production of acrylic acid derivative (I), or a by-product in the production of acrylic acid derivative (I).

The amount of acrylic acid derivative (I) contained in composition A may be, for example, within a range of 3 to 50 mass % or within a range of 5 to 20 mass %.

The amount of alcohol (II) contained in composition A may be, for example, within a range of 3 to 50 mass % or within a range of 5 to 20 mass %.

The amount of alcohol (II) contained in composition A may be, for example, 0.1 to 3 parts by weight or 0.3 to 2 parts by weight, per part by weight of acrylic acid derivative (I).

Composition A may further contain other components.

Step A

In step A, composition A containing acrylic acid derivative (I) and alcohol (II) is brought into contact with acid anhydride (III-0) to convert alcohol (II) into ester compound (IV).

The method for bringing composition A into contact with acid anhydride (III-0) is not particularly limited as long as alcohol (II) in composition A comes into contact with acid anhydride (III-0). The mode of this contact encompasses, for example, (a) adding acid anhydride (III-0) to composition A, and (b) generating composition A in the presence of acid anhydride (III-0).

Acid anhydride (III-0) may be an open-chain acid anhydride, or a cyclic acid anhydride.

Examples of acid anhydride (III-0) include
(a) carboxylic acid anhydrides,
(b) sulfonic acid anhydrides,
(c) anhydrides of carboxylic acid and sulfonic acid, and the like.

Specific examples of "(a) carboxylic acid anhydrides" include
(i) acetic anhydride, propionic anhydride, butyric anhydride, crotonic anhydride, benzoic anhydride, and like open-chain acid anhydrides;
(ii) succinic anhydride, glutaric anhydride, maleic anhydride, phthalic anhydride, 5,6-dihydroxy-1,4-dithiin-2,3-dicarboxylic anhydride, 5-norbornene-2,3-dicarboxylic anhydride, 1,2,3,6-tetrahydrophthalic anhydride, bicyclo[2.2.2]oct-5-ene-2,3-dicarboxylic anhydride, and like cyclic acid anhydrides; and
(iii) halides thereof.

Example of the halides include difluoroacetic anhydride, perfluoropropionic anhydride, 3,3,3-trifluoropropionic anhydride, pentafluoropropionic anhydride, 2,2,3,3,4,4-hexafluoropentanedioic anhydride, tetrafluorosuccinic anhydride, and trifluoroacetic anhydride.

Example of "(b) sulfonic acid anhydrides" include
(i) methanesulfonic anhydride, ethanesulfonic anhydride, propanesulfonic anhydride, butanesulfonic anhydride, pentanesulfonic anhydride, hexanesulfonic anhydride, vinylsulfonic anhydride, benzenesulfonic anhydride, and like open-chain sulfonic acid anhydrides;
(ii) 1,2-ethanedisulfonic anhydride, 1,3-propanedisulfonic anhydride, 1,4-butanedisulfonic anhydride, 1,2-benzenedisulfonic anhydride, and like cyclic sulfonic acid anhydrides; and
(iii) halides thereof.

Examples of open-chain acid anhydrides include compounds represented by Formula (III-0a):

$$R^a\text{—}X^a\text{—}O\text{—}X^b\text{—}R^b \qquad \text{(III-0a)}$$

wherein
$R^a$ represents monovalent hydrocarbon that may be substituted with one or more halogen atoms,
$X^a$ represents carbonyl or sulfonyl,
$X^b$ represents carbonyl or sulfonyl, and
$R^b$ represents monovalent hydrocarbon that may be substituted with one or more halogen atoms.

Example of "(c) anhydrides of carboxylic acid and sulfonic acid" include
(i) acetic methanesulfonic anhydride, acetic ethanesulfonic anhydride, acetic propanesulfonic anhydride, propionic methanesulfonic anhydride, propionic ethanesulfonic anhydride, propionic propanesulfonic anhydride, and like open-chain acid anhydrides;
(ii) 3-sulfopropionic anhydride, 2-methyl-3-sulfopropionic anhydride, 2,2-dimethyl-3-sulfopropionic anhydride, 2-ethyl-3-sulfopropionic anhydride, 2,2-diethyl-3-sulfopropionic anhydride, 2-sulfobenzoic anhydride, and like cyclic acid anhydrides; and (iii) halides thereof.

Examples of the "monovalent hydrocarbon" in the "monovalent hydrocarbon that may be substituted with one or more halogen atoms" represented by $R^a$ or $R^b$ include $C_{1-10}$ alkyl, $C_{2-10}$ alkenyl, $C_{3-10}$ cycloalkyl, $C_{6-18}$ aryl, and $C_{7-20}$ arylalkyl.

Examples of the cyclic acid anhydrides include compounds represented by Formula (III-0c):

(III-0c)

wherein
$X^a$ represents carbonyl or sulfonyl,
$X^b$ represents carbonyl or sulfonyl, and
$R^5$ represents divalent hydrocarbon or heterocycloalkylene.

Example of "divalent hydrocarbon" represented by $R^5$ include $C_{1-10}$ alkylene, $C_{2-10}$ alkenylene, $C_{6-12}$ arylene, $C_{3-12}$ cycloalkylene, and $C_{3-12}$ cycloalkenylene.

The "heterocycloalkylene" represented by $R^5$ refers to a divalent cycloalkylene group in which at least one of the ring-constituting carbon atoms is substituted with one or more heteroatoms selected from the group consisting of sulfur, oxygen, and nitrogen.

Acid anhydride (III-0) is preferably a cyclic acid anhydride (in this specification, this cyclic acid anhydride may sometimes be referred to as "cyclic acid anhydride (III)"), and more preferably a compound represented by Formula (III-a):

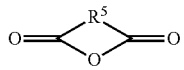

(III-a)

wherein $R^5$ represents divalent hydrocarbon.

$R^5$ is preferably $C_{2-20}$, more preferably $C_{2-10}$, and further more preferably $C_{2-6}$ divalent hydrocarbon.

$R^5$ is preferably ethane-1,2-diyl, ethene-1,2-diyl, or benzene-1,2-diyl, and particularly preferably ethane-1,2-diyl.

Acid anhydride (III-0) is particularly preferably succinic anhydride, maleic anhydride, or phthalic anhydride, and more particularly preferably succinic anhydride.

In the present invention, acid anhydride (III-0) may be a single kind, or a combination of two or more kinds of acid anhydride (III-0).

The amount of acid anhydride (III-0) used in step A is preferably within a range of 0.3 to 2.0 mol, more preferably within a range of 0.5 to 1.5 mol, and further more preferably within a range of 0.7 to 1.2 mol, per mol of alcohol (II). If the amount of acid anhydride (III-0) is overly small, the reaction in step A may not sufficiently proceed, possibly resulting in insufficient purification of acrylic acid derivative (I).

If the amount of acid anhydride (III-0) is overly large, removal of acid anhydride (III-0) may be required after step A.

The reaction temperature in step A is preferably within a range of 20 to 120° C., more preferably within a range of 40 to 100° C., and further more preferably within a range of 60 to 90° C.

If the reaction temperature is overly low, the reaction in step A may not sufficiently proceed, possibly resulting in insufficient purification of acrylic acid derivative (I).

An overly high reaction temperature is disadvantageous in terms of cost.

The reaction time in step A is not particularly limited as long as sufficient time is provided for the reaction in step A. Specifically, the reaction time may be, for example, within a range of 0.5 to 24 hours, within a range of 3 to 12 hours, or within a range of 5 to 9 hours.

If the reaction time is overly short, the reaction in step A may not sufficiently proceed, possibly resulting in insufficient purification of acrylic acid derivative (I).

An overly long reaction time is disadvantageous in terms of cost.

As stated above, in step A, acid anhydride (III-0) is reacted with alcohol (II) to generate ester compound (IV).

Therefore, when step A is performed, composition B containing acrylic acid derivative (I) and ester compound (IV) is obtained.

The amount of acrylic acid derivative (I) contained in composition B may be, for example, within a range of 1 to 30 mass %, 3 to 25 mass %, or 5 to 18 mass %.

The amount of ester compound (IV) contained in composition B may be within a range of 1 to 50 mass %, 10 to 40 mass %, or 20 to 30 mass %.

The weight ratio of ester compound (IV)/acrylic acid derivative (I) in composition B may be within a range of 0.1 to 8.0, within a range of 0.5 to 6.0, or within a range of 1.0 to 4.0.

The composition containing acrylic acid derivative (I) and ester compound (IV) in such amounts is suitably subjected to purification in step B below.

Composition B may further contain residual alcohol (II), and residual acid anhydride (III-0). In this case, however, the amounts thereof are preferably small.

Composition B may further contain residual other components (V).

Ester compound (IV) generated in step A may be a ring-opened form of cyclic acid anhydride (III), which is encompassed by acid anhydride (III-0).

For example, when cyclic acid anhydride (III) is phthalic anhydride, and alcohol (II) is methanol, the ester compound in a ring-opened form is 2-methoxycarbonylbenzoic acid.

Ester compound (IV) must have a boiling point higher than the boiling point of acrylic acid derivative (I). Ester compound (IV) has a boiling point at least 20° C. higher, more preferably at least 40° C. higher, and further more preferably at least 60° C. higher than the boiling point of acrylic acid derivative (I).

If the ester compound has such a boiling point, acrylic acid derivative (I) and the ester compound generated in step A are more easily separated by distillation in step B described below.

Ester compound (IV) is preferably flowable at a distillation temperature in step B below.

Step B

The method of the present invention may further suitably comprise step B.

In step B, acrylic acid derivative (I) and ester compound (IV) generated in step A are separated from each other by distillation.

The distillation in step B may be performed by using a general-purpose distillation device and a general-purpose distillation method. Preferable examples include a method that uses a distillation device provided with a stirrer, and a method that uses a thin-film distillation device.

In distillation in step B, acrylic acid derivative (I) may be recovered as a distillation fraction. In contrast, ester compound (IV) remains as a distillation residue in the distillation device, and can be arbitrarily discharged from the distillation device. In this manner, efficient purification of acrylic acid derivative (I) is possible while greatly reducing the incorporation of ester compound (IV).

The distillation temperature is preferably set between the boiling point of acrylic acid derivative (I) and the boiling point of ester compound (IV).

When composition B contains other components (V) having a boiling point higher than the boiling point of acrylic acid derivative (I) and lower than the boiling point of ester compound (IV), other components (V) can also be efficiently recovered in a manner similar to that for acrylic acid derivative (I). For example, when step B is carried out using a distillation column, other components (V) can be fractionated after the fractionation of acrylic acid derivative (I).

Examples of other components (V) include organic solvents other than alcohol (II).

The organic solvents other than alcohol (II) are preferably aprotic solvents.

Examples of the organic solvents other than alcohol (II) include amide solvents (e.g., dimethylacetamide (DMAc), dimethylformamide (DMF)), ether solvents (e.g., CPME, MTBE), sulfur-containing solvents (e.g., dimethylsulfoxide (DMSO)), and like heteroatom-containing organic solvents; and non-aromatic hydrocarbon solvents (e.g., hexane, pentane, cyclohexane), aromatic hydrocarbon solvents (e.g., toluene), and like carbon solvents.

Preferable examples of the organic solvents other than alcohol (II) include heteroatom-containing organic solvents.

More preferable examples of the organic solvents other than alcohol (II) include amide solvents and sulfur-containing solvents.

Specific preferable examples of the organic solvents other than alcohol (II) include dimethylacetamide, dimethylformamide, and dimethylsulfoxide.

More specific preferable examples of the organic solvents other than alcohol (II) include dimethylacetamide and dimethylformamide.

The organic solvents other than alcohol (II) may be a single kind, or a combination of two or more kinds.

The amount of other components (V) is not particularly limited, as long as the effects of the present invention are not significantly impaired. The amount may be, for example, within a range of 80 to 2100 parts by weight, 250 to 1600 parts by weight, or 400 to 1200 parts by weight, per 100 parts by weight of alcohol (II).

The amount of the organic solvents other than alcohol (II) is not particularly limited as long as the effects of the present invention are not significantly impaired. The amount may be, for example, within a range of 100 to 2000 parts by weight, 300 to 1500 parts by weight, or 500 to 1100 parts by weight, per 100 parts by weight of alcohol (II).

Other components (V) may be derived from composition A.

Specifically, to perform distillation using a distillation column in step B, composition B is placed into the distillation column, and a distillation operation is performed.

The pot temperature for distillation is set between the boiling point of acrylic acid derivative (I) and the boiling point of ester compound (IV).

This temperature varies depending on the pressure in the distillation. For example, when distillation is carried out under reduced pressure within a range of 1.5 to 15 KPa, the temperature may be, for example, within a range of 40 to 120° C., within a range of 50 to 90° C., or within a range of 60 to 80° C.

The following is a preferable embodiment: the column overhead temperature increases from the start of the distillation and becomes constant. A fraction obtained before the temperature becomes constant is discarded as an initial fraction. Thereafter, a fraction obtained while the column overhead temperature is constant is collected as a main fraction. Then, after the column overhead temperature starts to increase again, other components (V) (e.g., organic solvents, such as DMSO) having a boiling point higher than the boiling point of acrylic acid derivative (I) and lower than the boiling point of ester compound (IV) are recovered.

Reuse of recovered DMSO and other organic solvents is advantageous in terms of cost for the production method of the present invention.

For example, in the production method of the present invention, the recovery of the organic solvents (e.g., DMSO, DMF, DMAc) from composition A is preferably 10% or more, more preferably 20% or more, and further more preferably 30% or more.

Step B is preferably performed under a pressure preferably within a range of 0 to 1 atm, more preferably within a range of 0 to 0.3 atm, and further more preferably within a range of 0 to 0.1 atm.

In the present invention, some or all of alcohol (II) contained in composition A is eliminated.

The amount of alcohol (II) contained in composition A treated by using the purification method of the present invention (i.e., purified acrylic acid derivative (I)) is preferably less than 0.8 parts by weight, more preferably less than 0.6 parts by weight, and further more preferably less than 0.4 parts by weight, per part by weight of acrylic acid derivative (I).

Method for Producing Acrylic Acid Derivative (I)

The method for producing acrylic acid derivative (I) of the present invention encompasses purification of the acrylic acid derivative represented by Formula (I) by using the purification method of the present invention described in detail above.

Specifically, the method for producing acrylic acid derivative (I) of the present invention may be a production method that comprises step A and step B described above in regard to the method for purifying acrylic acid derivative (I) of the present invention.

EXAMPLES

The present invention is described below in more detail with reference to Examples. However, the present invention is not limited to these Examples.

Example 1 (Purification of Methyl Methacrylate)

A composition containing 43.1 parts by weight of methanol, 56.9 parts by weight of methyl methacrylate, and DMF as a solvent was prepared. Then, 1.1 equivalent of succinic anhydride (relative to the methanol amount) was added to the composition, followed by heating at 60° C. for 3 hours.

The reaction solution after the succinic anhydride treatment was subjected to GC analysis. The results revealed that methyl methacrylate was 23.7 parts by weight, methanol was 1.9 parts by weight, and succinic anhydride in a ring-opened form was 74.3 parts by weight. As is clear from these results, the succinic anhydride treatment significantly reduced the methanol content while generating succinic anhydride in a ring-opened form.

Example 2 (Purification of 2-Fluoroacrylic Acid Methyl Ester)

A composition containing 43.5 parts by weight of methanol, 56.5 parts by weight of 2-fluoroacrylic acid methyl ester, and DMF as a solvent was prepared. Then, succinic anhydride was added in the amount shown in Table 1 to the composition, followed by heating at 60° C. for 3 hours.

The reaction solution after the succinic anhydride treatment was subjected to GC analysis. Table 1 shows the results. The analytical values were calculated (GC area %), excluding DMF, which was a solvent. As is clear from the table, the succinic anhydride treatment significantly reduced the methanol content while generating succinic anhydride in a ring-opened form.

TABLE 1

| Succinic anhydride treatment (amount relative to methanol amount) | 2-Fluoroacrylic acid methyl ester | Methanol | Succinic anhydride in ring-opened form |
| --- | --- | --- | --- |
| None | 56.5% | 43.5% | 0.0% |
| Yes (1.1 equivalent amount) | 27.0% | 0.8% | 72.2% |
| Yes (0.9 equivalent amount) | 29.7% | 5.4% | 64.8% |
| Yes (0.8 equivalent amount) | 32.8% | 9.2% | 58.0% |

Example 3 (Distillation)

The reaction purification solution prepared in Example 2 was subjected to distillation under a reduced pressure of 1.5 to 15 kPa at a pot temperature of 70 to 80° C. using a distillation column to collect 2-fluoroacrylic acid methyl ester. As a control, the solution that was not treated with succinic anhydride was used.

The distillation fraction after distillation was subjected to GC analysis. Table 2 shows the composition. According to the GC analysis results, neither succinic anhydride nor succinic anhydride in a ring-opened form was present in the distillation fraction after distillation. As is clear from the table, when the reaction solution was distilled (i.e., when succinic anhydride treatment was carried out), a distillation fraction in which the amount ratio of 2-fluoroacrylic acid methyl ester to methanol was very high was obtained.

TABLE 2

| Succinic anhydride treatment (amount relative to methanol amount) | 2-Fluoroacrylic acid methyl ester | Methanol |
| --- | --- | --- |
| None | 56.9 parts by weight | 43.1 parts by weight |
| Yes (1.1 equivalent amount) | 94.7 parts by weight | 5.3 parts by weight |
| Yes (0.9 equivalent amount) | 84.2 parts by weight | 15.8 parts by weight |
| Yes (0.8 equivalent amount) | 78.5 parts by weight | 21.5 parts by weight |

Subsequently, distillation conditions were adjusted to 20 mmHg and 90 to 100° C., and DMF was recovered from the distillation fraction.

Table 3 shows the recovery rate of DMF.

As is clear from Table 3, when succinic anhydride treatment was carried out, DMF was collected with an extremely high recovery rate.

TABLE 3

| Succinic anhydride treatment (amount relative to methanol amount) | DMF remained in distillation fraction after DMF recovery | Recovered DMF (DMF recovery) | DMF in residue on distillation |
| --- | --- | --- | --- |
| None | 15.9% | 26.4% | 57.7% |
| Yes (1.1 equivalent amount) | 1.0% | 71.2% | 27.8% |
| Yes (0.9 equivalent amount) | 0.9% | 68.4% | 30.8% |
| Yes (0.8 equivalent amount) | 0.7% | 69.6% | 29.7% |

Example 4

2-Fluoroacrylic acid methyl ester was purified and the solvent was collected in a manner similar to that described in Examples 2 and 3 using 1.1 equivalent of succinic anhydride relative to methanol, except that DMSO or DMAc was used as a solvent, in place of DMF. Table 4 shows the results. As is clear from Table 4, even when DMSO or DMAc was used as a solvent, the solvent was collected with an extremely high recovery rate.

TABLE 4

| Solvent | Succinic anhydride treatment (amount relative to methanol amount) | Solvent remained in distillation fraction after solvent recovery | Recovered solvent (solvent recovery) | Solvent in residue on distillation |
| --- | --- | --- | --- | --- |
| DMSO | Yes (1.1 equivalent amount) | 0.9% | 71.4% | 27.7% |
| DMAc | Yes (1.1 equivalent amount) | 1.2% | 71.0% | 27.8% |

The invention claimed is:

1. A method for purifying an acrylic acid derivative represented by Formula (I):

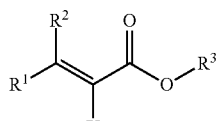

(I)

wherein

R$^1$ and R$^2$ are identical or different, and each represents alkyl, fluoroalkyl, aryl that may have one or more substituents, halogen, or hydrogen, R$^3$ represents alkyl, fluoroalkyl, aryl that may have one or more substituents, or hydrogen, and X represents alkyl, fluoroalkyl, halogen, or hydrogen,
the method comprising
step A of bringing a composition A containing the acrylic acid derivative represented by Formula (I) and alcohol represented by Formula (II):

$R^4$—OH, wherein $R^4$ represents alkyl, fluoroalkyl, or aryl that may have one or more substituents, into contact with an acid anhydride to convert the alcohol into an ester compound that has a boiling point higher than the boiling point of the acrylic acid derivative represented by Formula (I).

2. The method according to claim 1, further comprising step B of separating the acrylic acid derivative represented by Formula (I) and the ester compound by distillation.

3. The method according to claim 1, wherein $R^1$ represents hydrogen, $C_{1-20}$ alkyl, or $C_{1-20}$ fluoroalkyl.

4. The method according to claim 1, wherein $R^2$ represents hydrogen, $C_{1-20}$ alkyl, or $C_{1-20}$ fluoroalkyl.

5. The method according to claim 1, wherein $R^3$ represents $C_{1-20}$ linear alkyl.

6. The method according to claim 1, wherein X represents $C_{1-20}$ alkyl, fluorine, chlorine, or hydrogen.

7. The method according to claim 1, wherein $R^4$ represents $C_{1-6}$ alkyl.

8. The method according to claim 1, wherein the acid anhydride is a cyclic acid anhydride.

9. The method according to claim 8, wherein the acid anhydride is a compound represented by Formula (III-a):

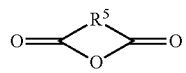

(III-a)

wherein $R^5$ represents divalent hydrocarbon.

10. The method according to claim 9, wherein the acid anhydride is succinic anhydride or phthalic anhydride.

11. The method according to claim 1, wherein the composition A further contains a heteroatom-containing organic solvent, and wherein a composition B containing the acrylic acid derivative represented by Formula (I) and the heteroatom-containing organic solvent is obtained after the separation in step B.

12. The method according to claim 11, wherein the heteroatom-containing organic solvent is separated and recovered from the composition B.

13. A method for producing an acrylic acid derivative represented by Formula (I):

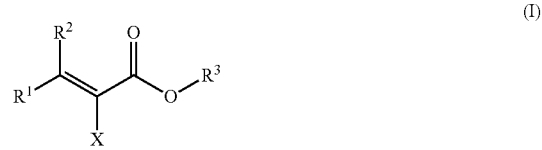

(I)

wherein $R^1$ and $R^2$ are identical or different, and each represents alkyl, fluoroalkyl, aryl that may have one or more substituents, halogen, or hydrogen, $R^3$ represents alkyl, fluoroalkyl, aryl that may be substituted with one or more substituents, or hydrogen, and X represents alkyl, fluoroalkyl, halogen, or hydrogen, the method comprising purifying the acrylic acid derivative represented by Formula (I) by the purification method of claim 1.

* * * * *